US011454561B2

(12) United States Patent
Jamali

(10) Patent No.: US 11,454,561 B2
(45) Date of Patent: Sep. 27, 2022

(54) 3D CONTACT FORCE SENSING

(71) Applicant: Silicon Microstructures, Inc., Milpitas, CA (US)

(72) Inventor: Armin Jamali, Milpitas, CA (US)

(73) Assignee: MEASUREMENT SPECIALTIES, INC., Hampton, VA (US)

( * ) Notice: Subject to any disclaimer, the term of this patent is extended or adjusted under 35 U.S.C. 154(b) by 209 days.

(21) Appl. No.: 16/513,561

(22) Filed: Jul. 16, 2019

(65) Prior Publication Data

US 2020/0284675 A1    Sep. 10, 2020

Related U.S. Application Data

(60) Provisional application No. 62/813,683, filed on Mar. 4, 2019.

(51) Int. Cl.
*G01L 7/18* (2006.01)

(52) U.S. Cl.
CPC .............. *G01L 7/182* (2013.01); *G01L 7/185* (2013.01)

(58) Field of Classification Search
CPC ....................................................... G01L 7/182
See application file for complete search history.

(56) References Cited

U.S. PATENT DOCUMENTS

| 10,383,543 | B2 | 8/2019 | Bonyak et al. |
| 2002/0055674 | A1 | 5/2002 | Ben-Haim et al. |
| 2006/0169060 | A1* | 8/2006 | Okada ............... G01L 5/165 73/862.043 |
| 2008/0009750 | A1 | 1/2008 | Aeby et al. |
| 2010/0094163 | A1 | 4/2010 | Deladi et al. |
| 2013/0274712 | A1* | 10/2013 | Schecter ............... A61B 18/02 604/510 |

FOREIGN PATENT DOCUMENTS

| WO | 2018150314 A1 | 8/2018 |
| WO | WO-2018150314 A1 * | 8/2018 ......... A61B 18/1492 |

OTHER PUBLICATIONS

Tacticath Quartz Contact Force Ablation Catheter, Clinical Compendium, [online], Abbott, 2019, [retrieved on Jan. 14, 2020], Retrieved from the Internet: <URL: https://www.sjm.com/en/professionals/featured-products/electrophysiology/therapy/irrigated-ablation-catheters/tacticath-quartz-contact-force-ablation-catheter?clset=af584191-45c9-4201-8740-5409f4cf8bdd%3ab20716c1-c2a6-4e4c-844b-d0dd6899eb3a>, 16 pages.

(Continued)

*Primary Examiner* — Paul M. West
*Assistant Examiner* — Mark A Shabman

(57) ABSTRACT

Contact-force-sensing systems that can provide additional information about the forces that are applied by catheters and other devices to cell walls and other surfaces. One example can provide directional information for a contact-force-sensing system. For example, magnitude, plane angle, and off-plane angle information can be provided by a contact-force-sensing system. Another example can provide guiding functionality for a contact-force-sensing system. For example, a contact-force-sensing system can provide tactile response to a surgeon or operator to allow a device to be accurately guided though a body.

20 Claims, 16 Drawing Sheets

(56) References Cited

OTHER PUBLICATIONS

St. Jude Medical Receives FDA Approval of TactiCath Quartz Contact Force Ablation Catheter, YouTube Video, St. Jude Medical, Oct. 27, 2014, [online], [retrieved on Jan. 14, 2020], Retrieved from the Internet <URL: https://www.youtube.com/watch?v=HG_crLG9w7c>, 1 page.
New Interface—TactiCath Contact Force Ablation Catheter, YouTube Video, Endosense, Nov. 26, 2013, [online], [retrieved on Jan. 14, 2020], Retrieved from the Internet <URL: https://www.youtube.com/watch?v=aYvYO8Hpyig, 1 page.
Extended European Search Report, European Application No. 20160553.2- 1115, European Filing Date, Jun. 4, 2020.

* cited by examiner

3D CONTACT FORCE SENSING

CROSS-REFERENCES TO RELATED APPLICATIONS

This application claims priority to U.S. provisional application No. 62/813,683, filed Mar. 4, 2019, which is incorporated by reference.

BACKGROUND

Minimally invasive surgery has become an invaluable tool in the medical field in recent years. As compared to conventional surgery, minimally invasive surgery has reduced patient risks, improved outcomes, sped recovery times, and lowered costs.

Several techniques can be used in minimally invasive surgery. Often, a catheter can be directed through a cell wall or natural orifice and into a body, for example though the vascular system. Once the catheter is at a desired location, a specific surgical technique can be applied. For example, ablation using radio-frequency heating or liquid cooling, angioplasty using inflatable structures, drug delivery, and other techniques can be employed using a catheter and associated equipment and devices.

As part of these procedures, catheters and associated devices often come into contact with cell walls or other surfaces in the body. At such times, it can be important that a surgeon has an accurate reading of a force that is being applied to the cell wall or other structure by a catheter. For example, being able to prevent excessive force can help to prevent the cell wall from being ruptured. Also, providing insufficient force can be ineffective or can cause unwanted complications. Being able to provide the proper force can likewise ensure that enough force is applied during a procedure, such as an ablation, to ensure that desired results can be achieved.

Accordingly, contact force sensing has become a useful tool in minimally invasive surgery. Medical equipment can implement contact force sensors to determine how much force is being applied to a cell wall or other surface. But this knowledge is limited in its scope, and is therefore limited in its usefulness. That is, with just a single data point reflecting a contact force, a surgeon can have an inadequate vision of the nature and details of the contact between the catheter and cell wall.

Thus, what is needed are contact-force-sensing systems that can provide additional information about the forces that are applied by catheters and other devices to cell walls and other surfaces.

SUMMARY

Accordingly, embodiments of the present invention can provide contact-force-sensing systems that can provide additional information about the forces that are applied by catheters and other devices to cell walls and other surfaces. For example, embodiments of the present invention can provide directional information, that is, information regarding a direction in which is force is being applied by a surgical device. These and other embodiments of the present invention can also, or instead, provide information that can be used to guide a surgical device.

An illustrative embodiment of the present invention can provide directional information for a contact-force-sensing system. A plurality of pressure-sensor chambers can be peripherally located around a central axis of the contact-force-sensing system. A force-receiving structure designed to come into direct contact with a cell wall can be included and can be located in or along the central axis. The force-receiving structure can be, or can include, a rod, ball or other structure. The force-receiving structure can include or be coupled to a force-distribution structure that distributes the force received by the force-receiving structure to the peripherally-located pressure-sensor chambers. Each of these pressure-sensor chambers can contain a fluid. This fluid can be compressible, or it can be incompressible. A pressure sensor can be located in, or associated with, each of the pressure-sensor chambers. The resulting pressures can be used to determine not only the magnitude of the force applied to the force-receiving structure, but the angle of the force as well. For example, these and other embodiments of the present invention can be used to determine the magnitude, plane angle, and off-plane angle of the force encountered by the force-receiving structure.

These and other embodiments of the present invention can employ different numbers of peripherally-located pressure-sensor chambers. For example, two, three, four, five, or more than five peripherally-located pressure-sensor chambers can be employed.

These and other embodiments of the present invention can employ one or more centrally-located pressure-sensor chambers along with one or more peripherally-located pressure-sensor chambers. These centrally-located pressure-sensor chambers can be located along the central axis of the contact-force-sensing system. In these systems, a force-receiving structure can act directly on a centrally-located pressure-sensor chamber. The centrally-located pressure-sensor chamber can then be used to determine a magnitude of the force experienced by the force-receiving structure, while the peripherally-located pressure-sensor chambers can be used to determine direction information.

These and other embodiments of the present invention can employ a centrally-located pressure-sensor chamber, where the centrally-located pressure-sensor chamber surrounds or encompasses one or more peripherally-located pressure-sensor chambers. For example, the peripherally-located pressure-sensor chambers can be balloons. The centrally-located pressure-sensor chamber can be a balloon that encompasses or surrounds the other balloons. The larger, central balloon can be filled with cold liquid for cryogenics. It can also or instead be used to convey radio-frequency or other energy for local heating.

These and other embodiments of the present invention can provide guiding functionality for a contact-force-sensing system. For example, a contact-force-sensing system can provide tactile response to a surgeon or operator to allow a device to be accurately guided through a body. The device can be a surgical tool, imaging device, or other device. The system can include two devices coupled to each other through a catheter. A distal or remote end can include a guiding tip. The guiding tip can be directed in an up-down, right-left manner in order to guide the remote end to a desired location. The guiding tip can be directed by a number of peripherally-located pressure-sensor chambers. For example, an increase in a top pressure-sensor chamber can cause the guiding tip to angle downward. The pressure in the peripherally-located pressure-sensor chambers can be controlled by corresponding peripherally-located pressure-sensor chambers located at a near or proximal end of the catheter. The pressure in the proximate pressure-sensor chambers can be controlled by a joystick or other control manipulated by a surgeon or other operator. For example, changes in the position of the joystick can change pressures in the proximate pressure-sensor chambers, which can couple to, or be formed as part of, the distal pressure-sensor chambers. This can cause changes in pressure in the remote pressure-sensor chambers, thereby changing the angle of the guiding tip. In this way, changes in joystick position can result in changes in guiding tip orientation, thereby allowing the remote end of the catheter to be guided to a destination. In these and other embodiments of the present invention, the guide tip can be held in place and can thus be used as a force-receiving structure. This can allow the device to be used as a 3D force sensing system once the destination has been reached.

These and other embodiments of the present invention can be applied to catheters, nasogastric tubes, endoscopes, laparoscopes, and other such devices that are now used, as well as other devices that can be developed in the future.

Various embodiments of the present invention can incorporate one or more of these and the other features described herein. A better understanding of the nature and advantages of the present invention can be gained by reference to the following detailed description and the accompanying drawings.

DESCRIPTION OF ILLUSTRATIVE EMBODIMENTS

Embodiments of the present invention can provide contact-force-sensing systems that provide information beyond contact magnitude to a surgeon. For example, embodiments of the present invention can provide directional information regarding forces encountered by a contact-force-sensing system. These and other embodiments of the present invention can also, or instead, provide contact-force-sensing systems that deliver guidance information. An example of a contact force sensing system that can provide directional information shown in the following figure.

Figure 1:
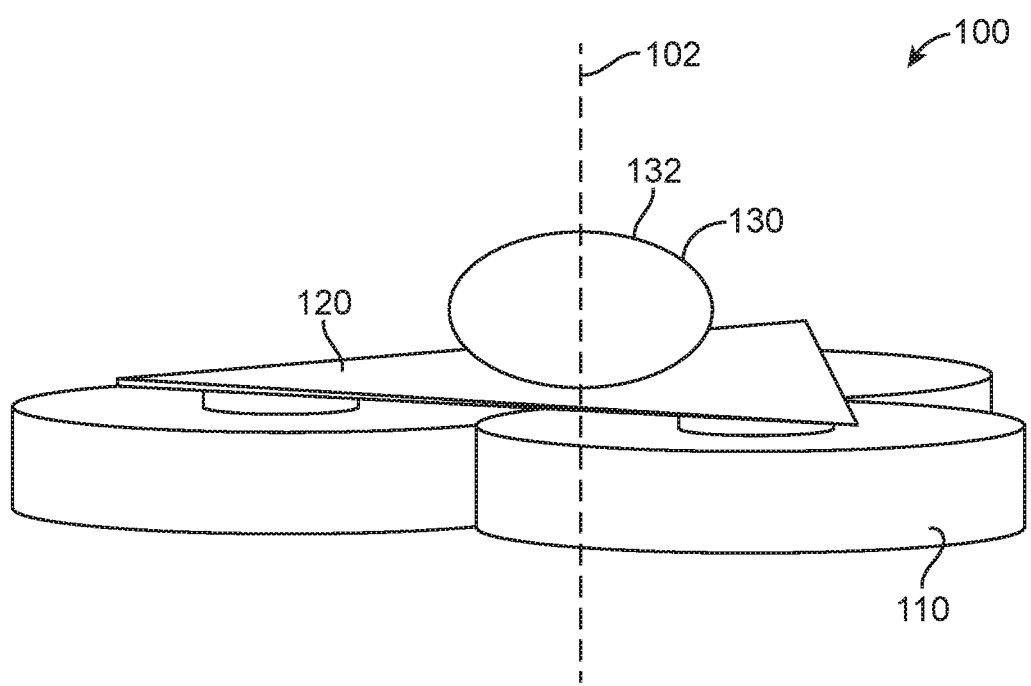
FIG. 1 illustrates a contact-force-sensing system according to an embodiment of the present invention.

FIG. 1 illustrates a contact-force-sensing system according to an embodiment of the present invention. This figure, as with the other included figures, is shown for illustrative purposes and does not limit either the possible embodiments of the present invention or the claims.

Contact-force-sensing system 100 can include a number of peripherally-located pressure-sensor chambers 110. Pressure-sensor chambers 110 can be peripherally located about central axis 102. Contact-force-sensing system 100 can further include a centrally-located force-receiving structure 130. Force-receiving structure 130 can make direct contact with a cell wall or other surface. Forces acting upon force-receiving structure 130 can be distributed to the pressure-sensor chambers 110 through force-distribution structure 120. Force-distribution structure 120 can be attached to, or formed as part of, force-receiving structure 130, or force-distribution structure 120 and force-receiving structure 130 can be formed separately. Force receiving structure 130, and the other force receiving structures shown herein and consistent with other embodiments of the present invention, can be rigid or flexible. For example, these force receiving structures can be a rigid structure having a polymer coating.

Force-receiving structure 130 is shown as a sphere, but can instead be a rod, or it can include a rod, sphere, or other structure. Force-receiving structure 130 can include a top surface 132 that is appropriately shaped for encountering a cell wall or other surface. For example, top surface 132 can be smooth, rounded, or have other appropriate characteristics. Force-distribution structure 120 can be in contact with pressure-sensor chambers 110. Pressure-sensor chambers 110 can each be filled with a fluid and can include a pressure sensor. The fluid can be a compressible or incompressible fluid.

Forces acting on force-receiving structure 130 can be measured by the pressure sensors in each of the pressure-sensor chambers. In this example, forces applied to force-receiving structure 130 can be distributed to pressure-sensor chambers 110 by force-distribution structure 120. The forces applied to pressure-sensor chambers 110 can act upon the fluid inside pressure-sensor chambers 110. Forces acting on the fluid can be measured by the pressure sensors (not shown) in the individual pressure-sensor chambers 110

The combined magnitude of the pressures measured by the individual pressure sensors can provide an indication of the magnitude of the force acting on force-receiving structure 130. The differences between the magnitudes of the pressures measured by the individual pressure sensors can provide an indication of the angle of the force acting on force-receiving structure 130. These and other embodiments of the present invention can be used to determine the magnitude, plane angle, and off-plane angle of the net force encountered by force-receiving structure 130.

Again, these and other embodiments of the present invention can provide contact-force-sensing systems that can provide guidance information. An example is shown in the following figure.

Figure 2:
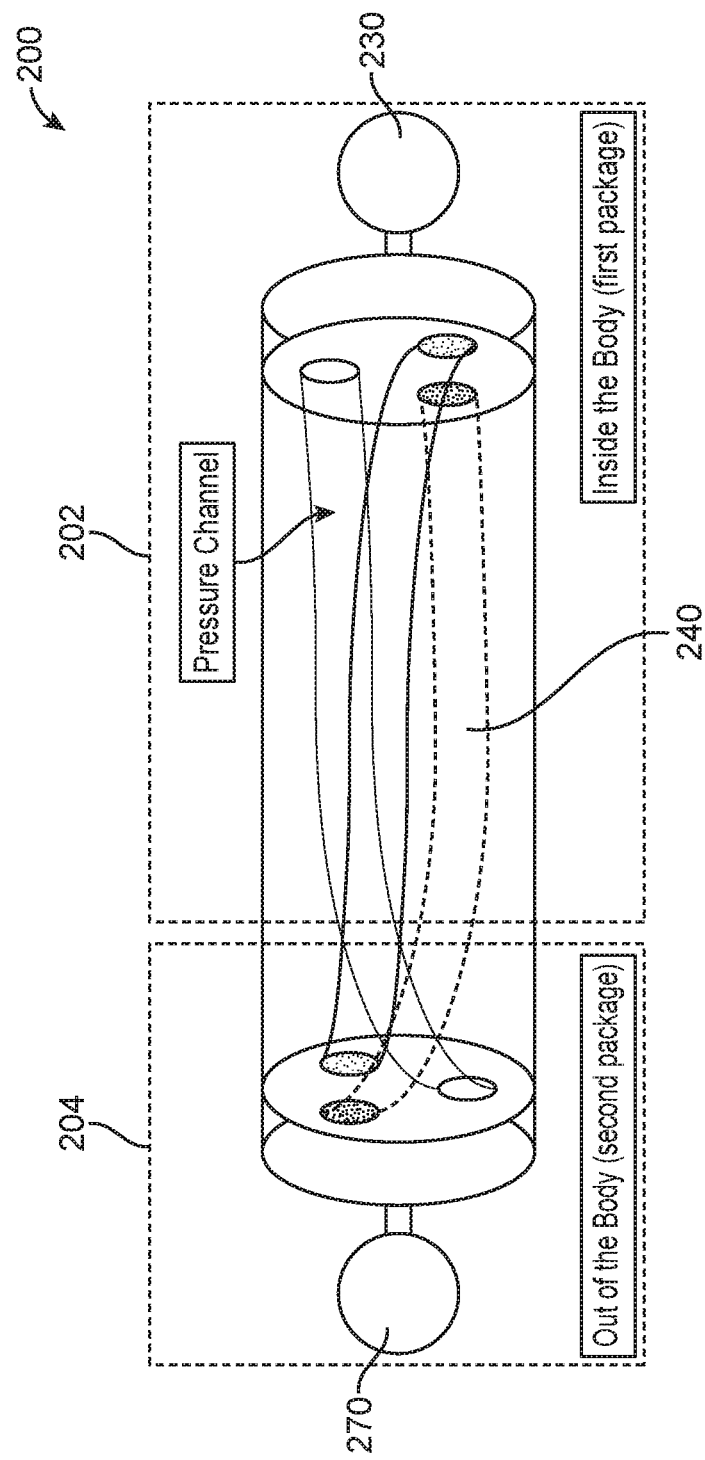
FIG. 2 illustrates a contact-force-sensing system that can provide guidance information according to an embodiment of the present invention.

FIG. 2 illustrates a contact-force-sensing system that can provide guidance information according to an embodiment of the present invention. Contact-force-sensing system 200 can include a remote or distal portion 202 that can be operational in a patient's body and a proximal portion 204 that can be operated by a surgeon. Contact-force-sensing system 200 can be used by a surgeon in guiding the distal portion 202 to a specific location.

Force-receiving structure 230 can be acted upon by forces as it encounters cell walls or other structures. Force-receiving structure 230 can act through a force-distribution structure (not shown) to apply pressure to fluids inside pressure channels 240. These fluids can receive compression or expansion forces depending on a direction of force applied to force-receiving structure 230. The compression or expansion forces on these fluids can generate forces that can be provided to joystick 270 through a force-distribution structure (not shown.) These resulting forces can drive joystick 270, which can provide a tactile response to a surgeon.

Similarly, a surgeon can provide a force to joystick 270. This force can be distributed to pressure channels 240 through a force distribution system. The resulting pressures in the pressure channels 240 can deliver a force to force-receiving structure 230 via a force-distribution structure. These forces can tilt force-receiving structure 230 for guidance purposes.

These two actions can allow a surgeon to receive a tactile response indicating a force received at a distal end by force-receiving structure 230, while allowing a surgeon to tilt force-receiving structure 230 up or down and side-to-side to guide it to a desired location. The tactile response that is received, and the guidance that is provided, can be amplified or attenuated. For example, a size of force-receiving structure 230 and a size of joystick 270 can be varied relative to each other. A larger joystick 270 can require more movement by a surgeon or other operator to move force-receiving structure 230 by a certain amount.

These and other embodiments of the present invention can provide other types of systems that can be guided. These systems can include sensors, such as pressure sensors for measuring a fluid inside a body, a camera for providing images inside a body, or other types of sensors. An example is shown in the following figure.

Figure 3:
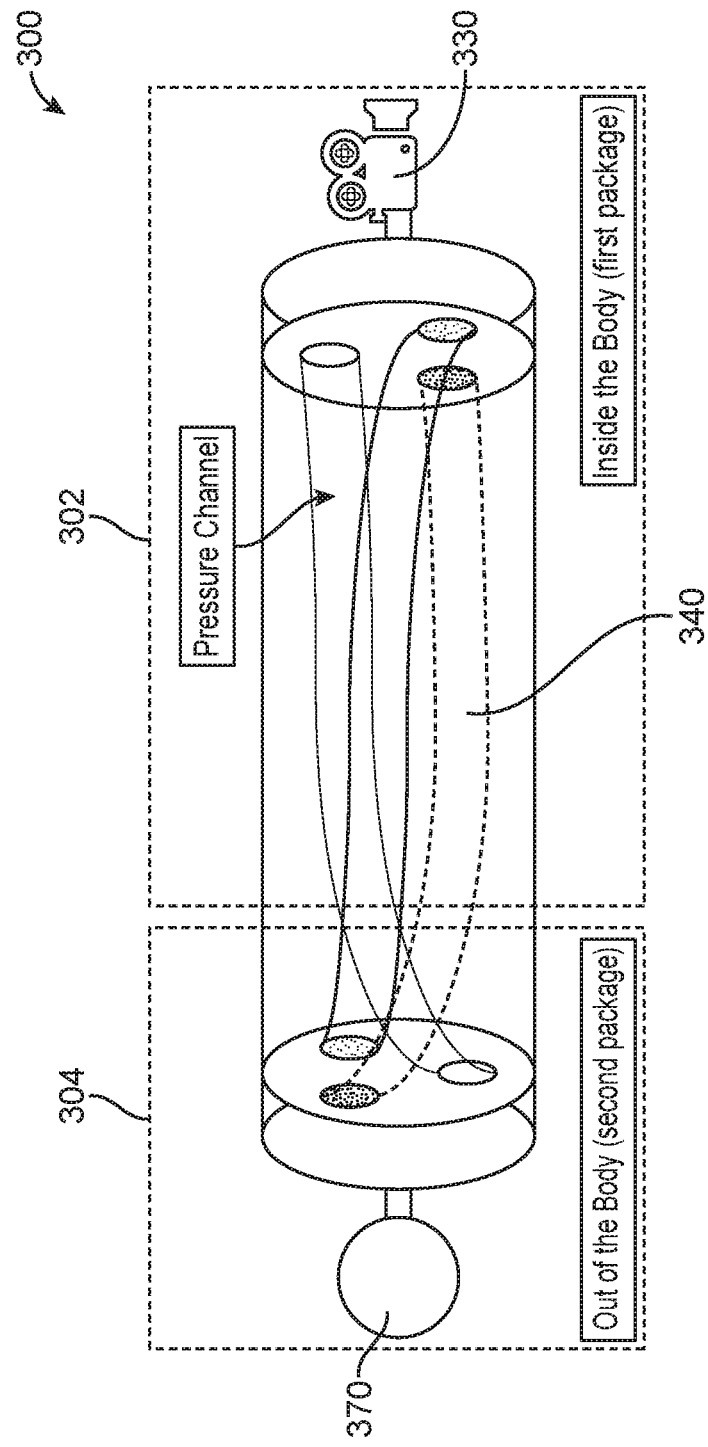
FIG. 3 illustrates a guided-sensor system according to an embodiment of the present invention.

FIG. 3 illustrates a guided-sensor system according to an embodiment of the present invention. Contact-force-sensing system 300 can include a remote or distal portion 302 that can be operational in a patient's body and a proximal portion 304 that can be operated by a surgeon. In this example, a surgeon can apply forces to joystick 370. These forces can be distributed by a force distribution system (not shown) to pressure channels 340. These forces can provide differences in pressures of fluids in pressure channels 340. These differences in pressures can provide forces that can act upon a force-distribution structure connected to camera sensor 330. In this way, a surgeon can provide forces on joystick 370 that can tilt or otherwise direct camera sensor 330. As a result, a surgeon or other operator can receive visual information in addition to tactile information. This configuration can also allow camera sensor 330 to rotate even in the absence of other movement by camera sensor 330. The guidance that is provided to camera sensor 330 by joystick 370 can be amplified or attenuated. For example, a size of joystick 370 can be varied. A larger joystick 270 can require more movement by a surgeon or other operator to move camera sensor 330 by a certain amount.

Figure 4:
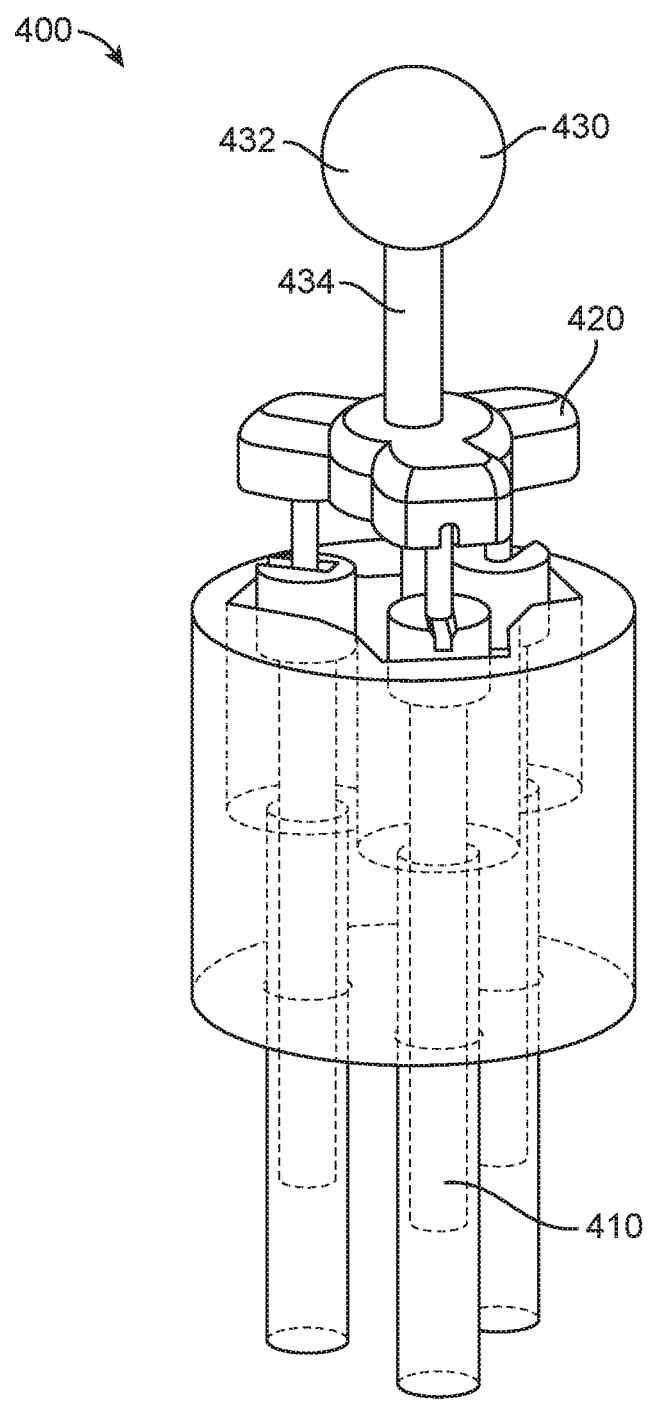
FIG. 4 illustrates a portion of a contact-force-sensing system according to an embodiment of the present invention.

FIG. 4 illustrates a portion of a contact-force-sensing system according to an embodiment of the present invention. Contact-force-sensing system 400 can include force-receiving structure 430. Force-receiving structure 430 can be located along a central axis of the contact-force-sensing system 400. Force-receiving structure 430 can include ball 432, which can be connected to rod 434. Contact-force-sensing system 400 can also include a number of peripherally-located pressure-sensor chambers 410. Forces received by force-receiving structure 430 can be distributed through force-distribution structure 420 to the individual pressure-sensor chambers 410. Pressure-sensor chambers 410 can be filled with a fluid. This fluid can be compressible or incompressible. Pressure-sensor chambers 410 can each include a pressure sensor. These pressure sensors can provide electrical signals to a computing device at an opposite and of a catheter or other medical device of which contact-force-sensing system 400 is included.

Accordingly, forces acting upon force-receiving structure 430 can be distributed to the pressure-sensor chambers 410 through force-distribution structure 420. Force-distribution structure 420 can increase or decrease a pressure of a fluid in the pressure-sensor chambers 410. These changes in pressures can be registered by the pressure sensors located in pressure-sensor chambers 410. These changes in pressure can be used by the computing device at the opposite end to determine magnitude and direction information for the forces acting on force-receiving structure 430. From this information, the magnitude, angle, plane angle, and off plane angle information for these forces can be determined.

Figure 5:
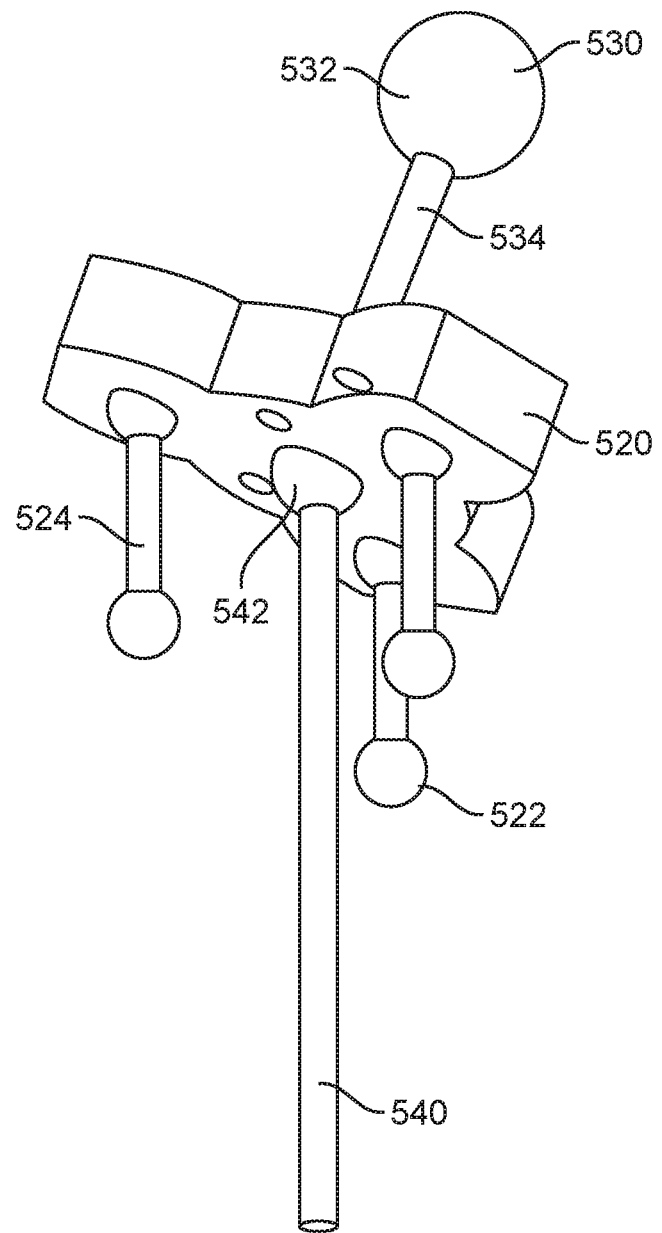
FIG. 5 illustrates another portion of a contact-force-sensing system according to an embodiment of the present invention.

FIG. 5 illustrates another portion of a contact-force-sensing system according to an embodiment of the present invention. This portion me include force-receiving structure 530 which can include a ball 532 and rod 534. Force-receiving structure 530 can be attached to force-distribution structure 520. Force-receiving structure 530 and force-distribution structure 520 can tilt about a central axis, defined in this example by rod 540. Force-distribution structure 520 can apply pressure to pressure-sensor chambers 410 (shown in FIG. 4) via rods 524. Rod 524 can include spherical structures 522 that can pivot in openings in force-distribution structure 520 and the individual pressure-sensor chambers 410. Similarly, Rod 540 can include spherical end 542 that can fit in an opening in force-distribution structure 520 to allow force-distribution structure 520 to tilt relative to rod 540.

Figure 6:
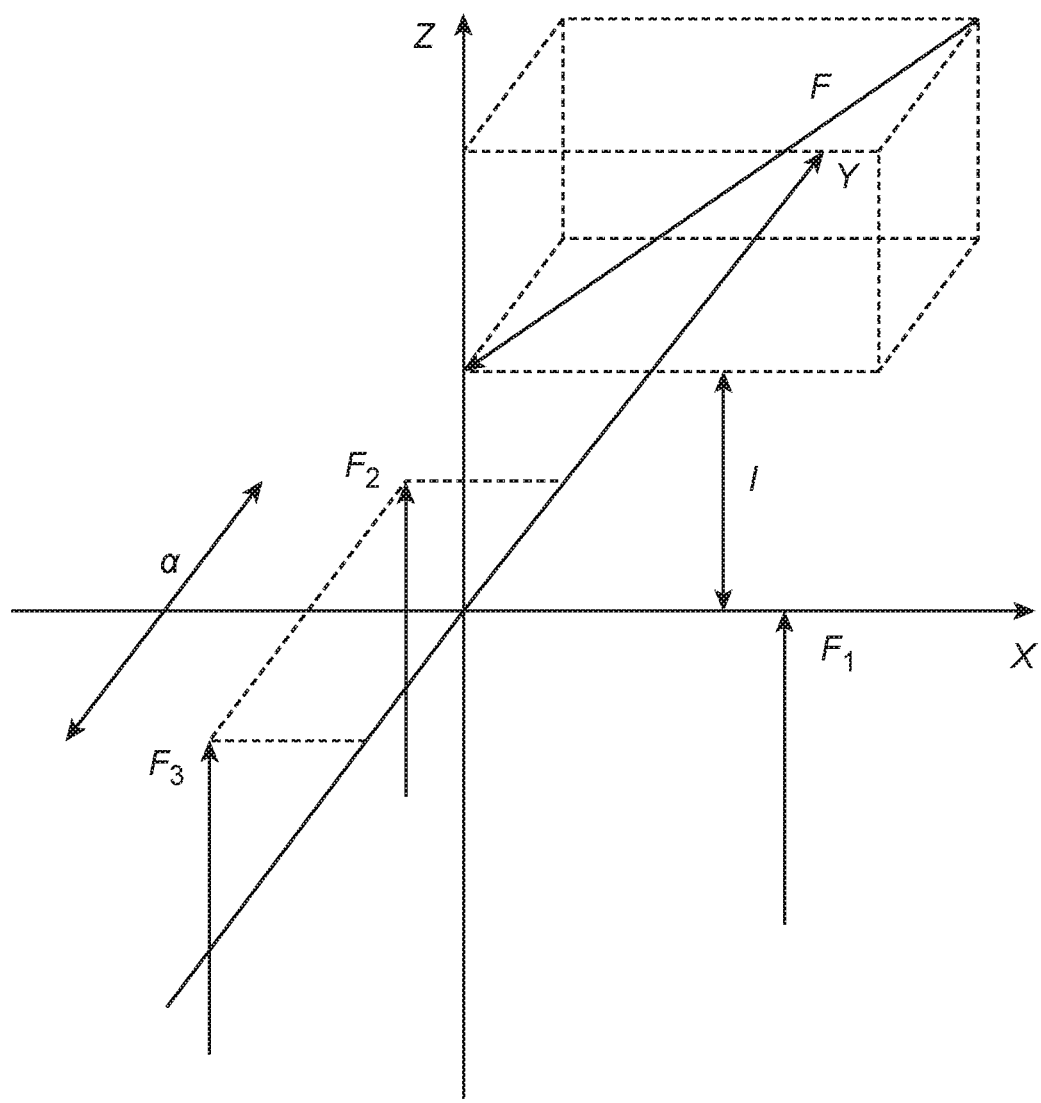
FIG. 6 illustrates an example of forces received by a contact-force-sensing system according to an embodiment of the present invention.

FIG. 6 illustrates an example of forces received by a contact-force-sensing system according to an embodiment of the present invention. In this example, forces F1, F2, and F3 can be inferred from changes in pressure sensors in pressure-sensor chambers. These changes in pressure can be used to determine a magnitude, angle, and off plane angle of the net force acting on a contact-force-sensing system.

Figure 7:
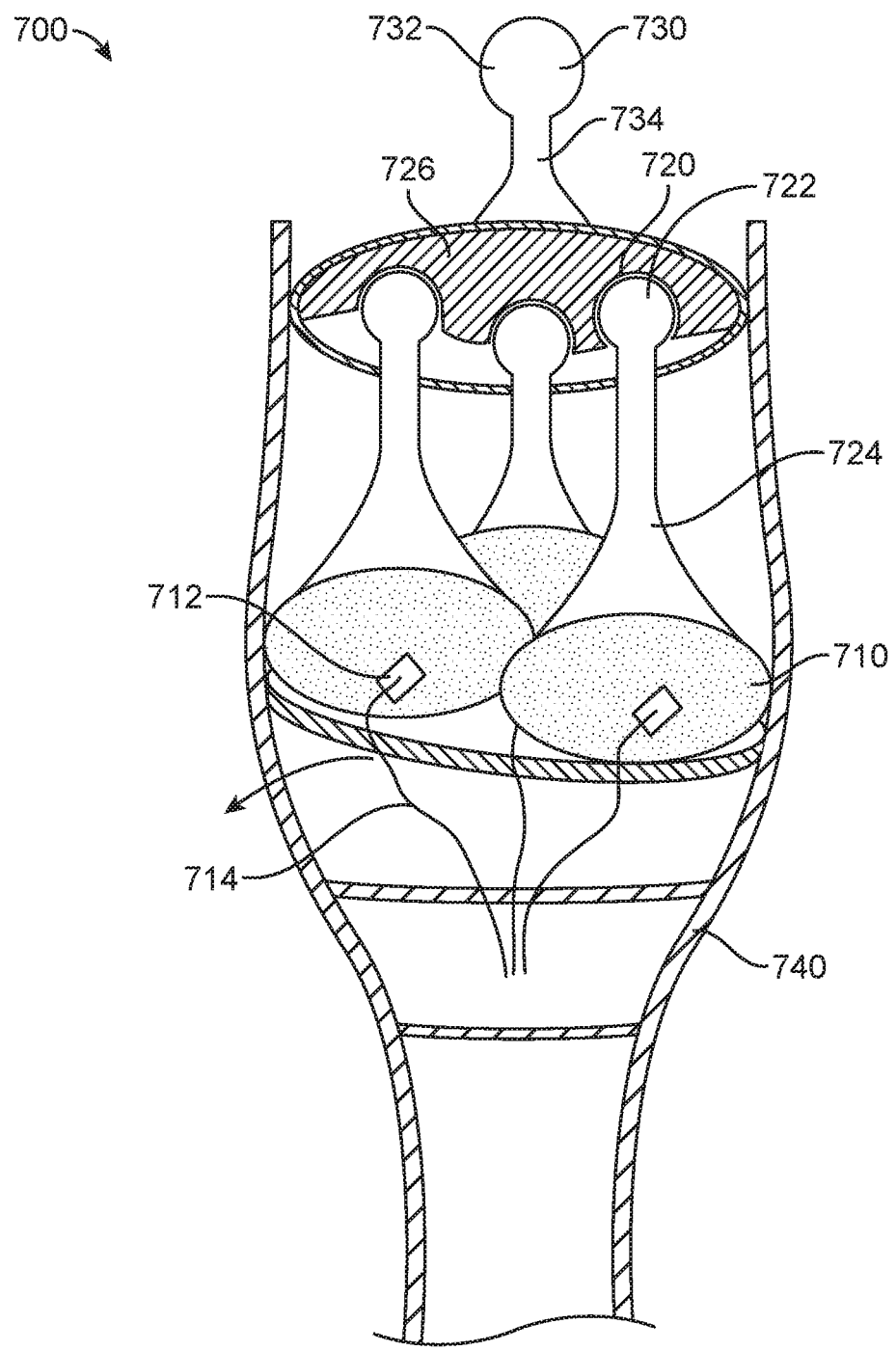
FIG. 7 illustrates another contact-force-sensing system according to an embodiment of the present invention.

FIG. 7 illustrates another contact-force-sensing system according to an embodiment of the present invention. In this example, contact-force-sensing system 700 can be housed in housing 740 and can include force-receiving structure 730 that can directly encounter a cell wall or other structure during use. Force-receiving structure 730 can include a spherical end 732 attached to a plate 726 of force-distribution structure 720 through rod 734. Force-distribution structure 720 can further include rods 724 which can be driven by plate 726 to act upon pressure-sensor chambers 710. Pressure-sensor chambers 710, along with the other pressure sensor chambers shown herein and other pressure sensor chambers consistent with embodiments of the present invention, can be at least partially filled with a fluid and can contain pressure sensors 712. These pressure sensor chambers can be at least partially filled with a deformable material, such as an elastic rubber or polymer. Pressure sensors 712 can be attached to a computing device through wires 714. As before, rods 724 can include spherical ends 722 that can reside in openings in plate 726 thereby allowing plate 726 to tilt relative to the central axis of force sensing system 700.

These and other embodiments of the present invention can employ a central pressure-sensor chamber along with a number of peripherally-located pressure-sensor chambers. This arrangement can come in various configurations. An example is shown in the following figure.

Figure 8:
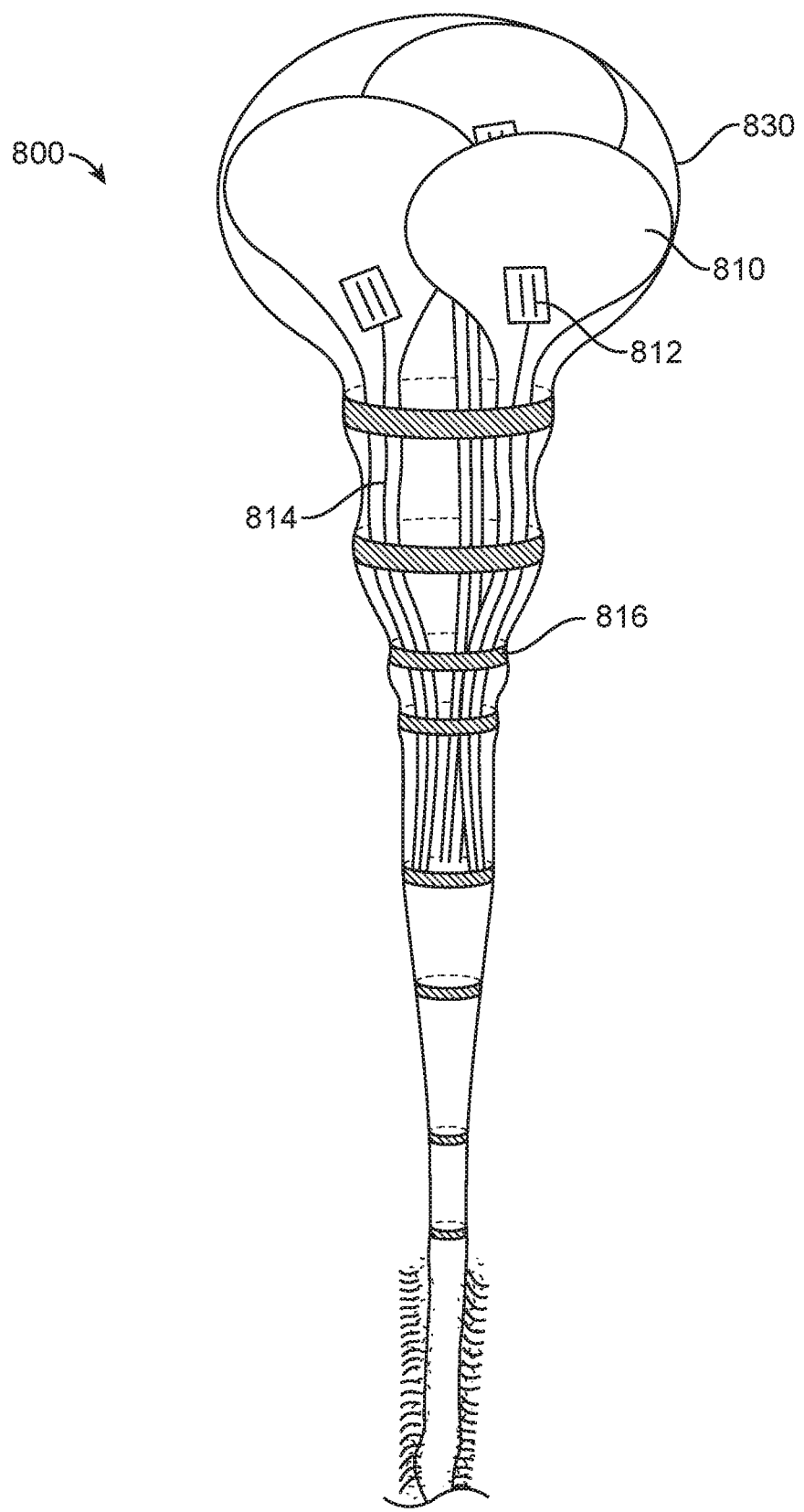
FIG. 8 illustrates another contact-force-sensing system according to an embodiment of the present invention.

FIG. 8 illustrates another contact-force-sensing system according to an embodiment of the present invention. In this example, pressure-sensor chambers 810 can be balloons that can be filled with a fluid, or an elastic or deformable material. Pressure-sensor chambers 810 can include pressure sensors 812 that can be attached to a remote computing device via wires 814. Pressure-sensor chambers 810 can be encased in a central pressure-sensor chamber 830. Electrodes 816 can be used to measure electrical signals of tissues that are encountered by this contact-force sensing system. Electrodes 816 can also or instead be used to apply currents, voltages, or both currents and voltages to these tissues. Electrodes 816 can be coupled to wires (not shown) that convey these signals to a distal end of this contact force sensing system.

This configuration can allow a central pressure-sensor chamber 830 to measure a magnitude of a force on the contact-force-sensing system 800, while the individual peripherally-located pressure-sensor chambers 810 provide directional information. This configuration can also allow central pressure-sensor chamber 830 to be formed of a material that can conduct radio-frequency signals for heating during ablation and other procedures. Central pressure-sensor chamber 830 can alternatively or also be filled with a cryogenic liquid for use during these and other procedures.

Figure 9:
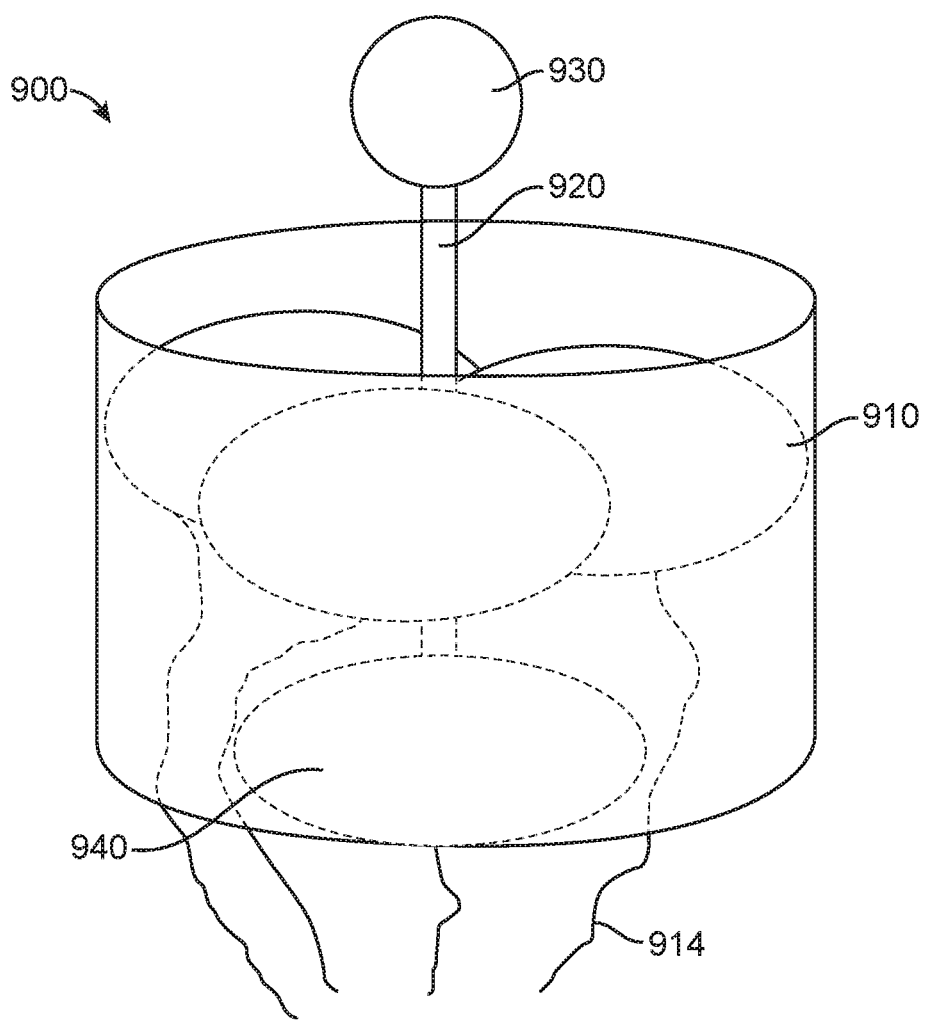
FIG. 9 illustrates another contact-force-sensing system according to an embodiment of the present invention.

FIG. 9 illustrates another contact-force-sensing system according to an embodiment of the present invention. In this example, contact-force-sensing system 900 can include a centrally-located pressure-sensor chamber 940 as well as a number of peripherally-located pressure-sensor chambers 910. The central and peripheral pressure-sensor chambers can each include a pressure sensor (not shown) which can be attached to a computer device through wires 914.

Forces can be received by force-receiving structure 930. These forces can be distributed through force-distribution structure 920 to the peripherally-located pressure-sensor chambers 910 and centrally-located pressure-sensor chamber 940. A vertical force complement along a central axis of contact-force-sensing system 900 can act directly on centrally-located pressure-sensor chamber 940. This force can apply a compression force to a fluid in centrally-located pressure-sensor chamber 940. This compression force can be measured by a pressure sensor and used in determining the magnitude of a force received by force-receiving structure 930. Lateral force components acting laterally on force-receiving structure 930 can push force-distribution structure 920 into one or more of the peripherally-located pressure-sensor chambers 910. This in turn can increase or decrease forces on fluids in pressure-sensor chambers 910, which can result in a difference of pressure being measured by their individual pressure sensors. This information can then be used by the remote computing device to determine directional information for the forces received by force-receiving structure 930.

Figure 10:
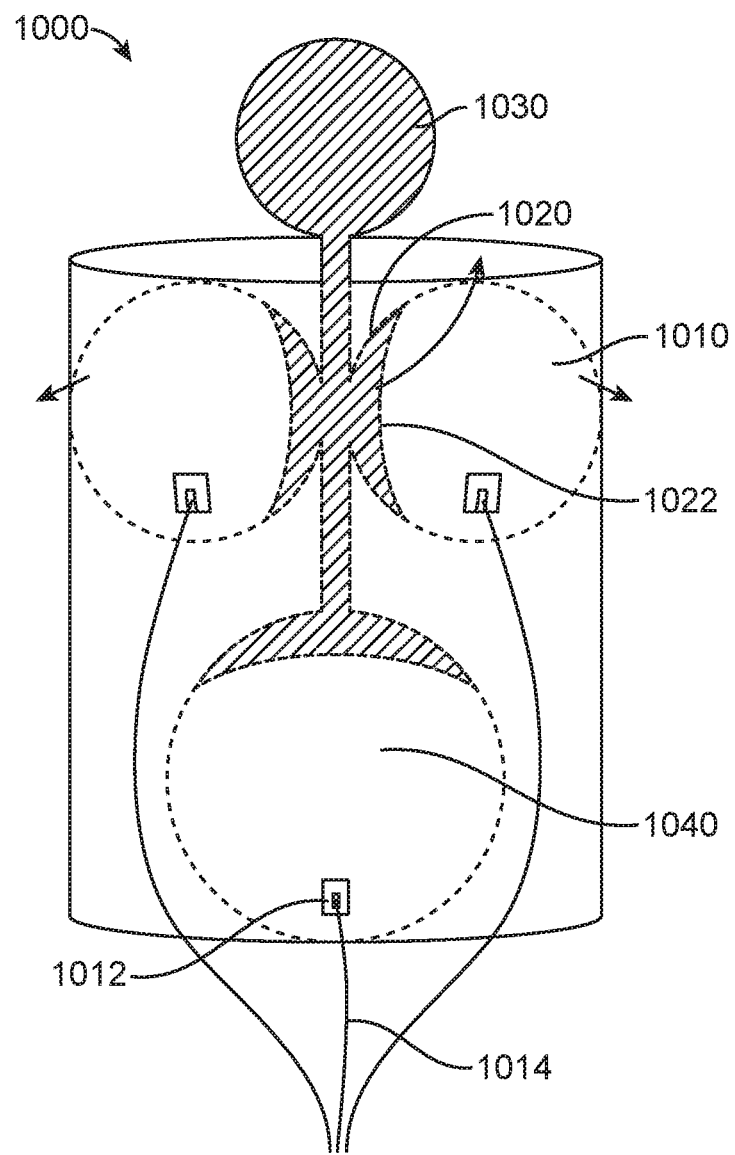
FIG. 10 illustrates another contact-force-sensing system according to an embodiment of the present invention.

FIG. 10 illustrates another contact-force-sensing system according to an embodiment of the present invention. In this example, contact-force-sensing system 1000 can include force-receiving structure 1030 that can be connected to force-distribution structure 1020. Force-distribution structure 1020 can include cupped services 1022 that can be adjacent to balloons acting as peripherally-located pressure-sensor chambers 1010 and centrally-located pressure-sensor chamber 1040. The peripherally located pressure-sensor chamber 1010 and centrally-located pressure-sensor chamber 1040 can include pressure sensors 1012 can communicate with a computing device over wires 1014.

The fluids in these various pressure-sensor chambers can be compressible or incompressible. For example, they can be water, coconut water, olive oil, or other fluids or combinations of these or other fluids. They can be completely filled with these fluids or they can include one or more air bubbles. Examples are shown in the following figures.

Figure 11:
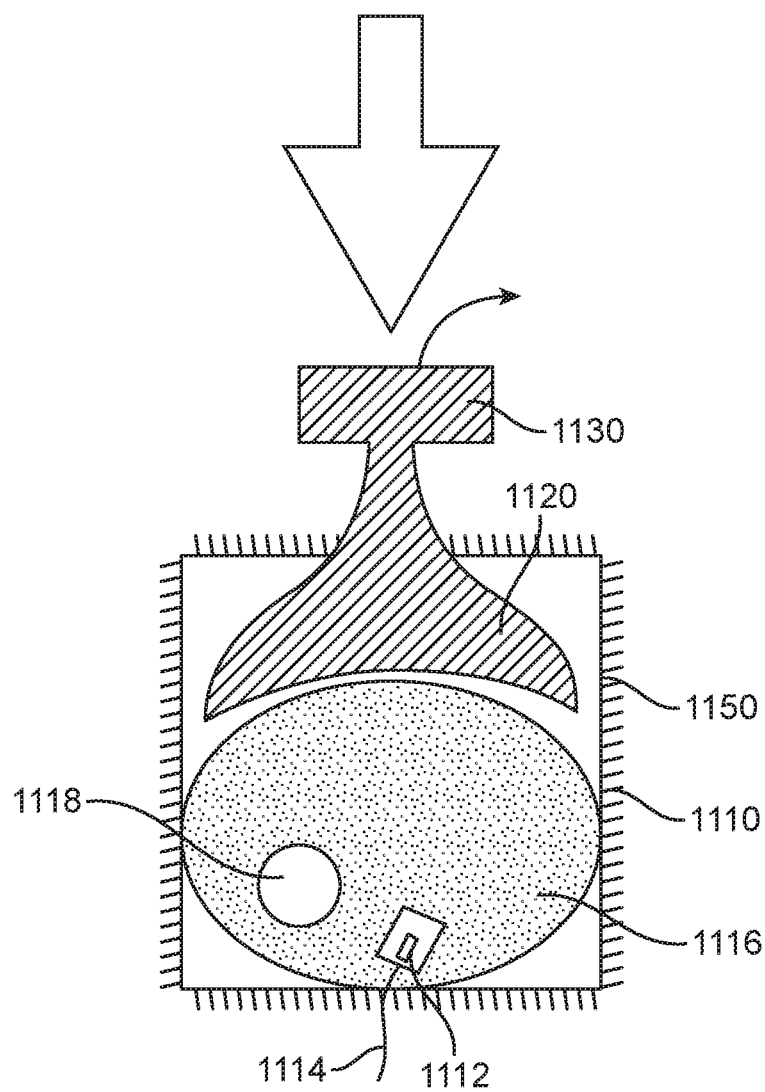
FIG. 11 illustrates a portion of a contact-force-sensing system according to an embodiment of the present invention.

FIG. 11 illustrates a portion of a contact-force-sensing system according to an embodiment of the present invention. This example includes a force-receiving structure 1130 coupled to a force-distribution structure 1120. Forces received at force-receiving structure 1130 can act through force-distribution structure 1120 on pressure-sensor chamber 1110. Pressure-sensor chamber 1110 can include a pressure sensor 1112 that can communicate with a remote computing device over wires 1114. Pressure-sensor chamber 1110 can be filled with a fluid 1116. The fluid can include one or more air bubbles 1118. Pressure-sensor chamber 1110 and a portion of force-distribution structure 1120 can be located in housing 1150. In this example, the use of one or more air bubbles 1118 and the optional use of a possible fluid can prevent damage from being done to a thin membrane of pressure sensor 1112 during use.

Figure 12:
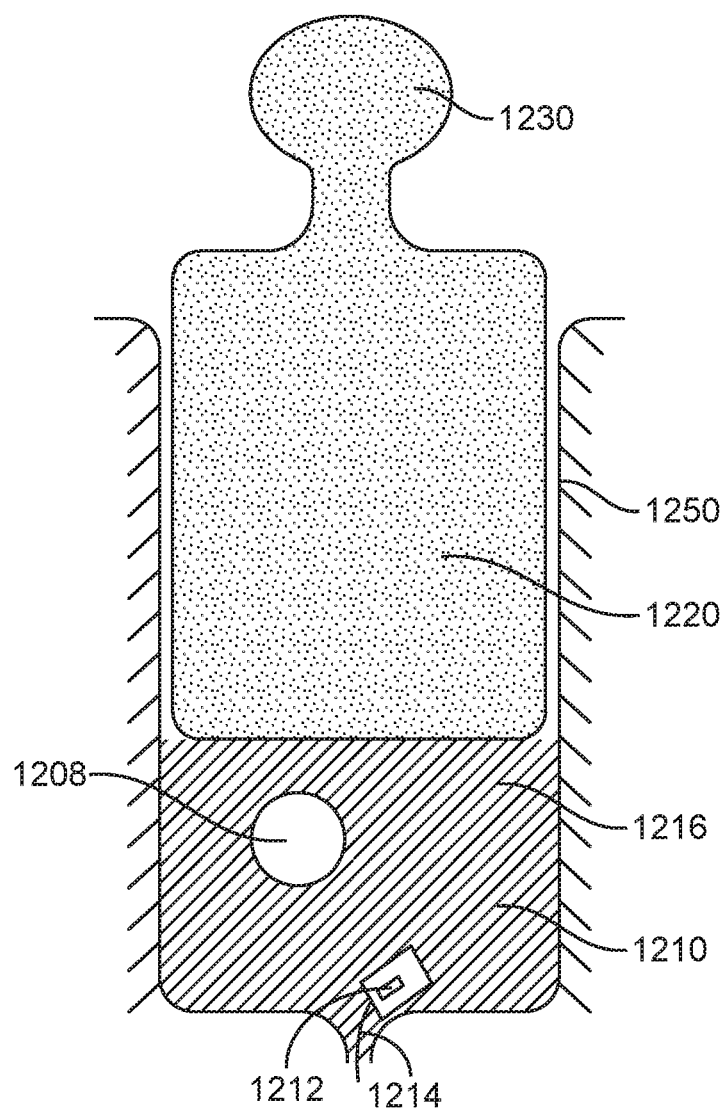
FIG. 12 illustrates a portion of a contact-force-sensing system according to an embodiment of the present invention.

FIG. 12 illustrates a portion of a contact-force-sensing system according to an embodiment of the present invention. This example includes a force-receiving structure 1230 coupled to a force-distribution structure 1220. Forces received at force-receiving structure 1230 can act through force-distribution structure 1220 on pressure-sensor chamber 1210. Pressure-sensor chamber 1210 can include a pressure sensor 1212 that can communicate with a remote computing device over wires 1214. Pressure-sensor chamber 1210 can be filled with a fluid 1216. The fluid can include one or more air bubbles 1218. Pressure-sensor chamber 1210 and a portion of force-distribution structure 1220 can be located in housing 1250. In this example, the use of one or more air bubbles 1218 and the optional use of a possible fluid can prevent damage from being done to a thin membrane of pressure sensor 1212 during use.

In these and other embodiments of the present invention, other compressible materials, such as rubber or elastomer can be used. An example is shown in the following figure.

Figure 13:
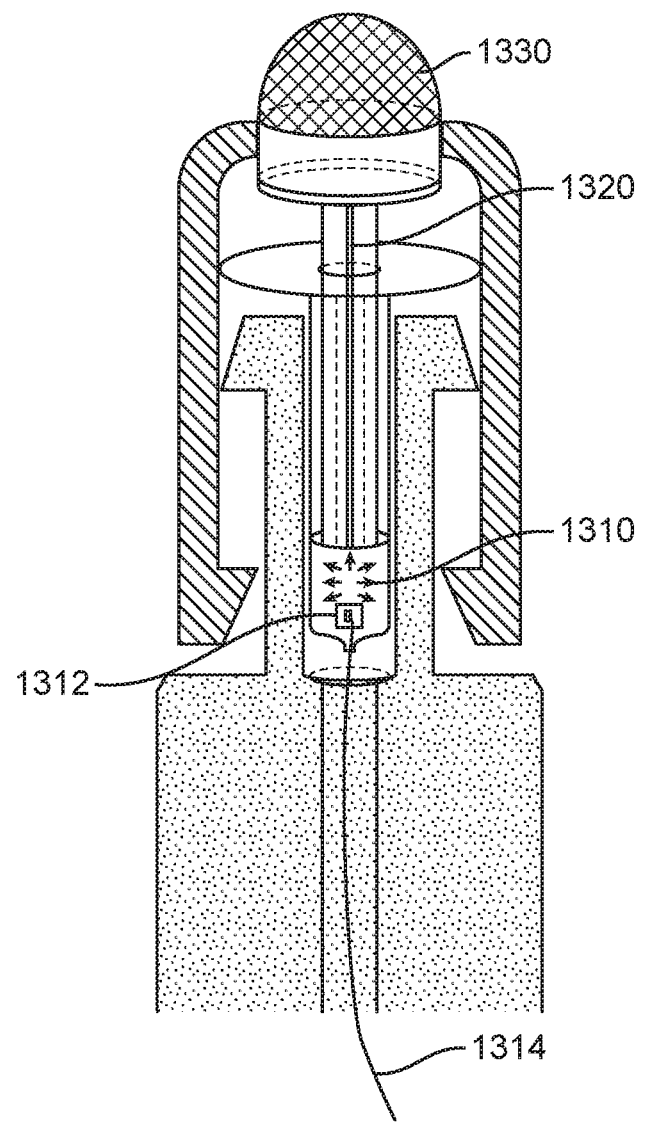
FIG. 13 illustrates a portion of a contact-force-sensing system according to an embodiment of the present invention.

FIG. 13 illustrates a portion of a contact-force-sensing system according to an embodiment of the present invention. This example includes a force-receiving structure 1330 which can apply force to a compressible material 1310 through a force-distribution structure 1320. Pressure sensor 1312 can be located in compressible material 1310 and can communicate with a remote computing device through wires 1314.

These and similar principles can be used in other types of force sensing structures. For example, these and other embodiments of the present invention can provide a device that can determine a distribution of a force. An example is shown in the following figure.

Figure 14:
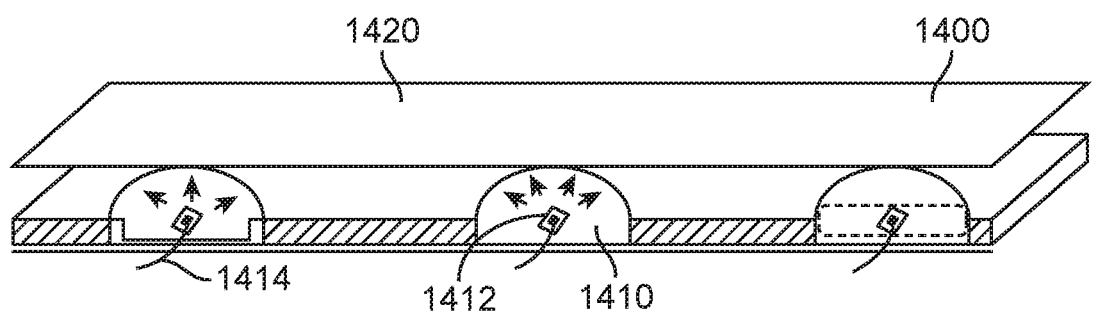
FIG. 14 illustrates a measuring device for determining a distribution of a force according to an embodiment of the present invention.

FIG. 14 illustrates a measuring device for determining a distribution of a force according to an embodiment of the present invention. Measuring device 1400 can include a number of pressure-sensor chambers 1410 housed in housing 1420. Forces acting upon housing 1420 may, in turn, act upon pressure-sensor chambers 1410. Pressure-sensor chambers 1410 can include pressure sensors 1412 that can communicate with a remote computing device over wires 1414. Pressure-sensor chambers 1410 can be arrayed in one or more dimensions to determine a distribution of a force acting upon housing 1420.

Figure 15:
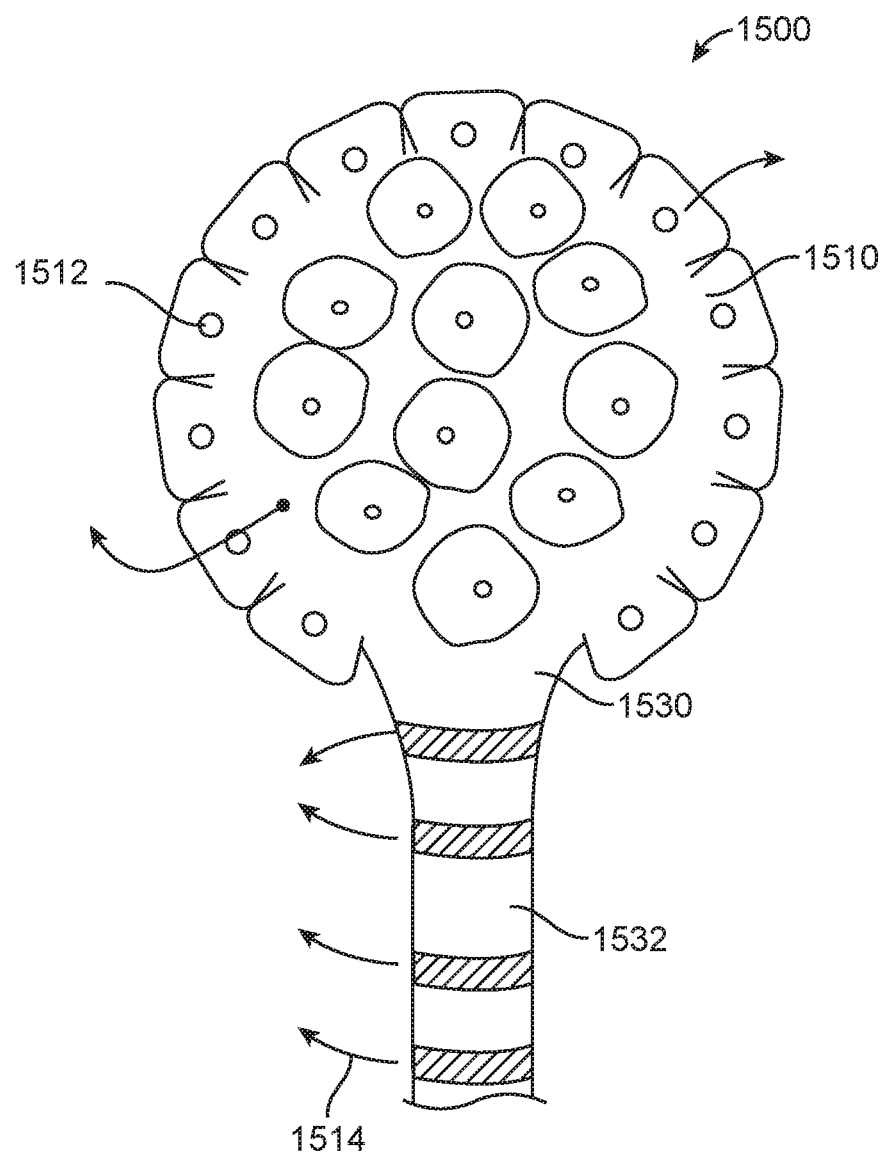
FIG. 15 illustrates another contact-force-sensing system according to an embodiment of the present invention.

FIG. 15 illustrates another contact-force-sensing system according to an embodiment of the present invention. Contact-force-sensing system 1500 can include a balloon or other structure 1530 supporting a number of pressure-sensor chambers 1510. Pressure-sensor chambers 1510 can be attached to a surface of structure 1530. Pressure-sensor chambers 1510 can each include a corresponding pressure sensor 1512. Pressure sensor 1512 can communicate with a remote computing device over wires and electrodes 1514. Structure 1530 can be supported by stem 1532.

In this embodiment of the present invention, pressure-sensor chambers 1510 can be attached to structure 1530. In these and other embodiments of the present invention, some or all of the pressure-sensor chambers 1510 can be formed by attaching a flexible layer over a structure. An example is shown in the following figure.

Figure 16:
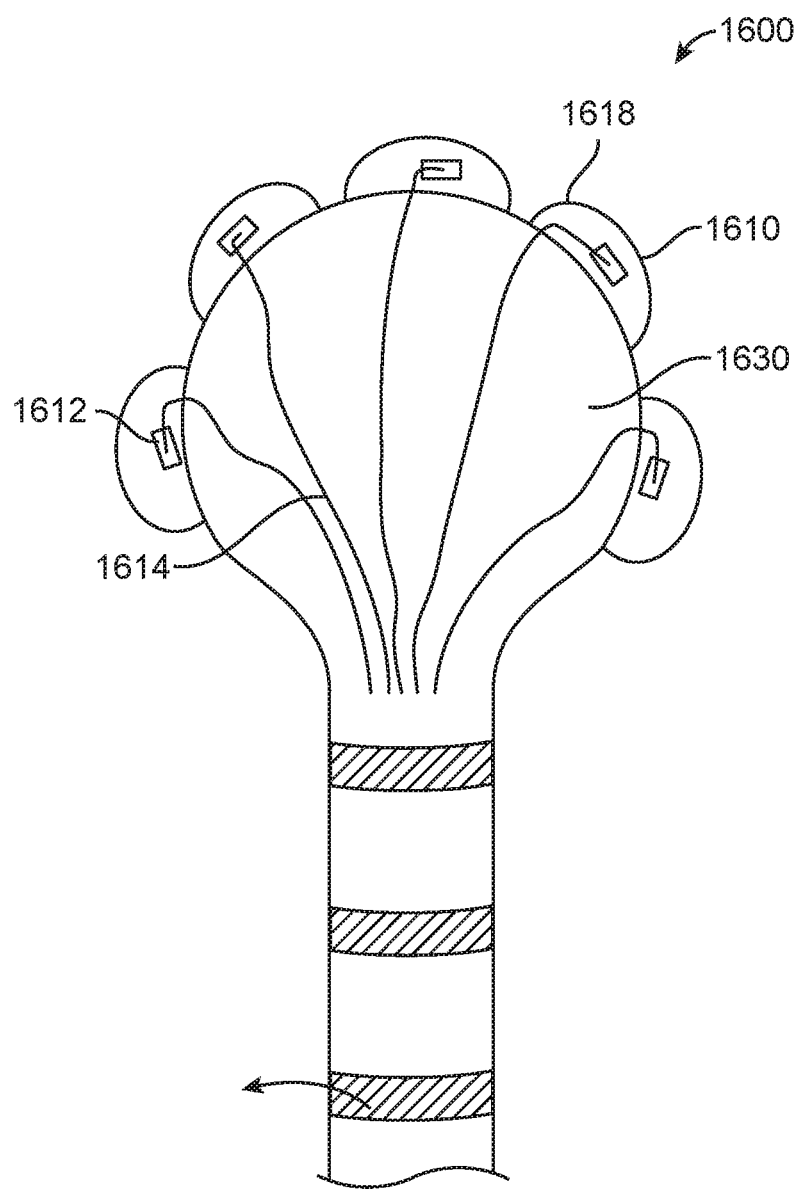
FIG. 16 illustrates another contact-force-sensing system according to an embodiment of the present invention.

FIG. 16 illustrates another contact-force-sensing system according to an embodiment of the present invention. Contact-force-sensing system 1600 can include structure 1630 supporting a number of pressure-sensor chambers 1610. Pressure-sensor chambers 1610 can be formed by placing flexible layer 1618 over a portion of a surface of structure 1630. Pressure-sensor chambers 1610 can include pressure sensors 1612, which can communicate with a remote computing device over wires and electrodes 1614.

The above description of embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated. Thus, it will be appreciated that the invention is intended to cover all modifications and equivalents within the scope of the following claims.

What is claimed is:

1. A force-measurement system comprising:
a central axis;
three or more discrete and independent pressure-sensor chambers placed radially around the central axis, each pressure-sensor chamber movable independently of a remainder of the pressure-sensing chambers and including a fluid housed in a chamber and a pressure sensor positioned to sense a pressure on the fluid; and
a central member in line with the central axis, the central member capable of being deflected in a least one direction.

2. The force-measurement system of claim 1, wherein the central member can be deflected about a central point, the central point in line with the central axis, and wherein when the central member is deflected the central member exerts a force on at least one of the three or more pressure-sensor chambers.

3. The force-measurement system of claim 1, wherein the force-measurement system is located at a distal end of a catheter.

4. The force-measurement system of claim 1, wherein the force-measurement system is located at a distal end of a nasogastric tube.

5. The force-measurement system of claim 1, wherein each pressure-sensor chamber is defined by an elastically deformable vessel.

6. The force-measurement system of claim 5, wherein each pressure-sensor chamber is at least partially filled with a liquid.

7. The force-measurement system of claim 6, wherein each pressure-sensor chamber is partially filled with air.

8. The force-measurement system of claim 5, wherein each pressure-sensor chamber is at least partially filled with a deformable solid material.

9. The force-measurement system of claim 5, wherein each vessel is elastically deformable without elastically deforming another one of the vessels.

10. A force-measurement system comprising:
three or more peripheral pressure-sensor chambers placed radially around a central axis of the force-measurement system, each peripheral pressure-sensor chamber comprising a fluid housed in a chamber and a pressure sensor positioned to sense a pressure on the fluid in the chamber;
a central rod to engage with a cell wall, the rod configured to be deflected;
a force-distribution structure attached to the rod and in contact with each of the three or more peripheral pressure-sensor chambers; and
a central balloon, wherein the three or more pressure-sensor chambers each comprises a balloon and the rod is configured to be deflected, wherein when the rod is deflected laterally, the rod exerts a force on at least one of the peripheral balloons, and when the rod is deflected along the central axis, the rod exerts a force on the central balloon.

11. The force-measurement system of claim 10, wherein the three or more peripheral pressure-sensor chambers each comprises a balloon.

12. The force-measurement system of claim 11, wherein the fluid in the balloons is an incompressible material.

13. The force-measurement system of claim 12, wherein the force-measurement system is located at a distal end of a catheter.

14. A force-measurement system comprising:
a central axis;
three or more pressure-sensor chambers comprising peripheral balloons placed radially around the central axis, each pressure-sensor chamber comprising a fluid housed in a chamber and a pressure sensor positioned to sense a pressure on the fluid; and
a central member comprising a central balloon in line with the central axis, the central member capable of being deflected in a least one direction, the peripheral balloons are located in the central balloon.

15. The force-measurement system of claim 14, wherein the central balloon is capable of being filled with a cryogenic material.

16. The force-measurement system of claim 14, wherein the central balloon is capable of emitting a radio-frequency signal.

17. The force-measurement system of claim 14, wherein the central member includes a rod, the rod configured to be deflected, wherein when the rod is deflected laterally, the rod exerts a force on at least one of the peripheral balloons, and when the rod is deflected along the central axis, the rod exerts a force on the central balloon.

18. The force-measurement system of claim 14, wherein the three or more pressure-sensor chambers each comprises a balloon.

19. The force-measurement system of claim 18, wherein the fluid in the balloons is a compressible material.

20. The force-measurement system of claim 18, wherein the fluid in the balloons is an incompressible material.

* * * * *